(12) United States Patent
Agarkov et al.

(10) Patent No.: US 10,588,732 B2
(45) Date of Patent: *Mar. 17, 2020

(54) MULTIPURPOSE IMPLANT WITH MODELED SURFACE STRUCTURE FOR SOFT TISSUE RECONSTRUCTION

(71) Applicant: IconLab USA, Inc., Aliso Viejo, CA (US)

(72) Inventors: Viacheslav Agarkov, Aliso Viejo, CA (US); Igor Uspenskiy, Nizhniy Novgorod (RU); Yury Kolmogorov, Nizhniy Novgorod (RU)

(73) Assignee: IconLab USA, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,805

(22) Filed: Oct. 31, 2016

(65) Prior Publication Data

US 2017/0112607 A1    Apr. 27, 2017

Related U.S. Application Data

(63) Continuation-in-part of application No. 14/323,891, filed on Jul. 3, 2014, now Pat. No. 9,480,777.

(Continued)

(30) Foreign Application Priority Data

Mar. 7, 2014   (RU) ............................... 2014108943

(51) Int. Cl.
*A61F 2/00* (2006.01)
*A61L 27/16* (2006.01)
*A61L 27/50* (2006.01)

(52) U.S. Cl.
CPC .......... *A61F 2/0063* (2013.01); *A61F 2/0077* (2013.01); *A61L 27/16* (2013.01);
(Continued)

(58) Field of Classification Search
None
See application file for complete search history.

(56) References Cited

U.S. PATENT DOCUMENTS 5,412,068 A   5/1995   Tang et al.
5,645,850 A   7/1997   Bezwada et al.
(Continued)

FOREIGN PATENT DOCUMENTS

EP   2 644 348 A1   10/2013

OTHER PUBLICATIONS

"Ethicon Physiomesh™ Flexible Composite Mesh" Sales Brochure (2012), downloaded from http://www.ethicon.com/sites/default/files/PHYSM-491-12-PHYSIOMESH-Sales-Brochure.pdf in 6 pages.

(Continued)

*Primary Examiner* — Isis A Ghali
(74) *Attorney, Agent, or Firm* — Buchaler, a professional corp.; Kari Barnes (57) ABSTRACT

Embodiments of a multi-purpose implant for use in surgery, such as for reconstruction of soft tissues, are disclosed. In some embodiments, the implant includes elastic polymer film made from a suitable biologically compatible polymer. The implant also includes a reinforcement element forms from a polyurethane mesh or other strong and stable woven or unwoven synthetic material. The reinforcement element can be fully enclosed by the film so that only the film comes into contact with the organs and tissues. Anti-adhesive properties or control over implant's integration into a body can be determined by the preset surface structure of the implant, while physical and mechanical properties, such as (Continued)

strength and elasticity of the implant, are obtained by virtue of reinforcement element geometry.

19 Claims, 6 Drawing Sheets

Related U.S. Application Data (60) Provisional application No. 61/979,895, filed on Apr. 15, 2014.

(52) U.S. Cl.
CPC ....... *A61L 27/50* (2013.01); *A61F 2002/0081* (2013.01); *A61L 2400/18* (2013.01); *A61L 2430/34* (2013.01)

(56) References Cited

U.S. PATENT DOCUMENTS

| | | | |
|---|---|---|---|
| 5,725,577 A | 3/1998 | Saxon | |
| 5,743,917 A | 4/1998 | Saxon | |
| 5,824,082 A | 10/1998 | Brown | |
| 6,113,623 A | 9/2000 | Sgro | |
| 6,180,848 B1 | 1/2001 | Flament et al. | |
| 6,224,894 B1 | 5/2001 | Jamiolkowski et al. | |
| 6,258,124 B1 | 7/2001 | Darois et al. | |
| 6,319,264 B1 | 11/2001 | Tormala et al. | |
| 6,383,201 B1 | 5/2002 | Dong | |
| 6,458,385 B2 | 10/2002 | Jamiolkowski et al. | |
| 6,551,356 B2 | 4/2003 | Rousseau | |
| 6,599,323 B2 | 7/2003 | Melican et al. | |
| 6,652,595 B1 | 11/2003 | Nicolo | |
| 6,669,735 B1 | 12/2003 | Pelissier | |
| 6,736,823 B2 | 5/2004 | Darois et al. | |
| 6,737,371 B1 | 5/2004 | Planck et al. | |
| 6,966,918 B1 | 11/2005 | Schuldt-Hempe et al. | |
| 6,969,400 B2 | 11/2005 | Rhee et al. | |
| 6,991,637 B2 | 1/2006 | Crawley et al. | |
| 7,094,261 B2 | 8/2006 | Zotti et al. | |
| 7,156,858 B2 | 1/2007 | Schuldt-Hempe et al. | |
| 7,594,921 B2 | 9/2009 | Browning | |
| 7,632,765 B2 | 12/2009 | Shalaby et al. | |
| 7,651,682 B2 | 1/2010 | Devore et al. | |
| 7,776,101 B2 | 8/2010 | Crawley et al. | |
| 7,785,334 B2 | 8/2010 | Ford et al. | |
| 7,789,888 B2 | 9/2010 | Bartee et al. | |
| 8,016,841 B2 | 9/2011 | Magnusson et al. | |
| 8,100,924 B2 | 1/2012 | Browning | |
| 8,119,742 B2 | 2/2012 | Dalsin et al. | |
| 8,206,632 B2 | 6/2012 | Rousseau et al. | |
| 8,287,909 B2 | 10/2012 | Martin et al. | |
| 8,308,699 B2 | 11/2012 | Zhang et al. | |
| 8,313,499 B2 | 11/2012 | Magnusson et al. | |
| 8,383,092 B2 | 2/2013 | Lee et al. | |
| 8,579,990 B2 | 11/2013 | Priewe | |
| 8,585,772 B2 | 11/2013 | Shalaby et al. | |
| 8,623,034 B2 | 1/2014 | Priewe | |
| 8,623,096 B2 | 1/2014 | Trabuco et al. | |
| 2002/0052654 A1 | 5/2002 | Darois et al. | |
| 2002/0147457 A1 | 10/2002 | Rousseau | |
| 2004/0181288 A1 | 9/2004 | Darois et al. | |
| 2005/0107868 A1 | 5/2005 | Nakayama et al. | |
| 2006/0095139 A1 | 5/2006 | Ricol et al. | |
| 2006/0142786 A1 | 6/2006 | Mathisen et al. | |
| 2006/0233852 A1 | 10/2006 | Milbocker | |
| 2006/0253203 A1 | 11/2006 | Alvarado | |
| 2006/0264698 A1 | 11/2006 | Kondonis et al. | |
| 2007/0129736 A1 | 6/2007 | Solecki | |
| 2007/0198040 A1 | 8/2007 | Buevich et al. | |
| 2007/0265710 A1 | 11/2007 | Brown et al. | |
| 2007/0276509 A1 | 11/2007 | Ratcliffe et al. | |
| 2008/0091222 A1 | 4/2008 | Deusch et al. | |
| 2008/0091276 A1 | 4/2008 | Deusch et al. | |
| 2008/0091277 A1 | 4/2008 | Deusch et al. | |
| 2008/0248086 A1 | 10/2008 | Asgari | |
| 2008/0299169 A1 | 12/2008 | Hoffman-Kim et al. | |
| 2008/0306497 A1 | 12/2008 | Brown et al. | |
| 2009/0005867 A1 | 1/2009 | Lefranc et al. | |
| 2009/0018559 A1 | 1/2009 | Buevich et al. | |
| 2009/0069826 A1 | 3/2009 | Walther et al. | |
| 2009/0192528 A1 | 7/2009 | Higgins et al. | |
| 2009/0234461 A1 | 9/2009 | Rehnke | |
| 2009/0248048 A1 | 10/2009 | Milbocker | |
| 2009/0270999 A1 | 10/2009 | Brown | |
| 2009/0304773 A1 | 12/2009 | Milbocker et al. | |
| 2010/0137903 A1 | 6/2010 | Lee et al. | |
| 2010/0152708 A1 | 6/2010 | Li et al. | |
| 2010/0228348 A1 | 9/2010 | McClain et al. | |
| 2010/0331995 A1 | 12/2010 | Smelt et al. | |
| 2011/0060420 A1 | 3/2011 | Bartee et al. | |
| 2011/0112561 A1 | 5/2011 | Mathisen et al. | |
| 2011/0202142 A1 | 8/2011 | Mao et al. | |
| 2011/0238094 A1 | 9/2011 | Thomas et al. | |
| 2011/0318395 A1 | 12/2011 | Martin et al. | |
| 2012/0003888 A1 | 1/2012 | Lee et al. | |
| 2012/0010635 A1 | 1/2012 | Yeretsian | |
| 2012/0053689 A1 | 3/2012 | Martin et al. | |
| 2012/0149849 A1 | 6/2012 | Dalsin et al. | |
| 2012/0165957 A1 | 6/2012 | Everland et al. | |
| 2012/0221118 A1 | 8/2012 | Bartee et al. | |
| 2013/0103157 A1 | 4/2013 | Kourtis et al. | |
| 2013/0110245 A1 | 5/2013 | Merklein et al. | |
| 2013/0165957 A1 | 6/2013 | Ciardelli et al. | |
| 2013/0218178 A1 | 8/2013 | Shandas et al. | |
| 2013/0267970 A1 | 10/2013 | Cardinale et al. | |
| 2013/0267971 A1 | 10/2013 | Liu et al. | |
| 2013/0317527 A1 | 11/2013 | Jacinto et al. | |
| 2014/0012395 A1 | 1/2014 | Soares Da Costa et al. | |

OTHER PUBLICATIONS

CN Brown and JG Finch "Which mesh for hernia repair?" *Ann R Coll Surg Engl* 92(4) pp. 272-278 (2010).

MULTIPURPOSE IMPLANT WITH MODELED SURFACE STRUCTURE FOR SOFT TISSUE RECONSTRUCTION

CROSS-REFERENCE TO RELATED APPLICATIONS

This application claims priority under 35 U.S.C. 111 as a continuation-in-part of U.S. application Ser. No. 14/323,891, filed Jul. 3, 2014, now U.S. Pat. No. 9,480,777, which claims priority to Russian Patent Application No. 2014108943, filed on Mar. 7, 2014, and U.S. Provisional Patent Application No. 61/979,895, filed on Apr. 15, 2014, each of which is incorporated by reference in their entirety.

BACKGROUND

Modern methods of soft tissue reconstruction call for the simultaneous use of materials that frequently have several incompatible properties. For example, in treating ventral hernia through the intra-peritoneal on-lay mesh method (laparoscopic IPOM), the synthetic implant material should ensure anti-adhesion on the visceral side (facing the internal organs). On the parietal side (facing the abdominal wall) it is desirable to ensure the tissue's controllable integration into the implant. The growing tissues should not shrink or crimple the implant in the distant post-operation period. At the same time, the tissue integration should reliably secure it to the abdominal wall tissue.

The porous structure of the implant surface should also meet criteria. For instance, macrophage cells and neutrophils, killers of bacteria, are unable to penetrate fine pores measuring less than 10 μm. This enables the bacteria, smaller than 1 μm, to form colonies in pores measuring less than 10 μm and in spaces of multi-filament meshes, which causes a risk of infection. Therefore it is desirable for the implant to have a structure in which the pores and gaps in the mesh plexus nodes would not be below 75 μm. See C N Brown, J G Finch "Which mesh for hernia repair?", Ann R Coll Surg Engl. 2010 May, available at http://www.ncbi.nlm.nih.gov/pmc/articles/PMC3025220/. It is desirable that the synthetic implant should have a minimum tissue response and be strong and elastic enough for clinical applications. It is desirable that the implant should be able to be sutured or fastened with a surgical stapler. The strength of the implant should be commensurable to the stress sustained by the abdominal wall during coughing, jumping, etc. (e.g., tensile strength up to 32 N/cm). At the same time, the implant should feature elasticity close to that of the abdominal wall (e.g., up to 38% at the maximum stress).

The task of creating such an implant has not been fulfilled since the implants known to date do not provide all of the desired capabilities.

Currently available implants contain layers of different non-absorbable materials fastened together by some means. In most cases, the layer that ensures integration of the abdominal wall tissues is a polypropylene or polyester mesh whilst the layer that provides the anti-adhesive barrier is made from polytetrafluoroethylene or, for instance, collagen. Such designs are described in the following patents and publications: U.S. Pat. No. 6,258,124 titled "Prosthetic repair fabric", U.S. Pat. No. 6,652,595 titled "Method of repairing inguinal hernias", U.S. Pat. No. 5,743,917 titled "Prosthesis for the repair of soft tissue defects", U.S. Patent Publication No. 20020052654 titled "Prosthetic repair fabric", U.S. Pat. No. 8,206,632 titled "Method of making composite prosthetic devices having improved bond strength", and U.S. Pat. No. 8,623,096 titled "Double layer surgical prosthesis to repair soft tissue," the entirety of each is hereby incorporated by reference.

Implants are available that are essentially in the form of a mesh from a stable strong material (polypropylene, polyester or other) coated with a temporary absorbable anti-adhesive material. The mesh is designed for soft tissues to grow into it whilst the absorbable layer, separating the mesh from visceral tissues, creates a temporary anti-adhesive barrier promoting the formation of peritoneum and minimizing the probability of union with the mesh during the wound healing. Following the biological degradation of the barrier, the mesh integrates into the abdominal wall tissue.

Such designs are described in the following publications: U.S. Patent Publication No. 20130317527 titled "Single plane tissue repair patch having a locating structure", U.S. Patent Publication No. 20130267971 titled "Single plane tissue repair patch", and U.S. Patent Publication No. 20130267970 titled "Single plane tissue repair patch," the entirety of each is hereby incorporated by reference. An example of commercial use of such a design is an implant under the trade name of PHYSIOMESH manufactured by ETHICON, Inc.

All these implants feature strength that ensures a high restorative effect and are fit for suture-aided fixation, but are disadvantageous in some aspects.

By virtue of its micro-porous structure, polytetrafluoroethylene mollifies the gravity and reduces the commissural side effects of the healing process, but does not altogether eliminate them. The use of collagen implies a high risk of a tissue rejection, allergic response or infection.

Another disadvantage is the shrinkage of the implant, which is specific to materials known to date (polypropylene, polyester). Growing through the mesh, the organism tissues contribute to its extra shrinkage and wrinkling, which negatively impacts the quality of the patient's life.

It is not recommended to introduce implants coated with a temporary absorbable anti-adhesive material in the event of a casual or scheduled opening of the digestive tract lumen or in the event of infection of the site since this may result in the infection of the implant itself, as its absorbable material promotes colonization of microorganisms, which may trigger a post-operative pyoinflammatory process.

These implants have either a mesh-like or porous structure, which ensures integration of the abdominal wall tissues, but makes it impossible to control the size of the mesh pore and cell. The material structure is usually determined by the range of pore and cell size. In woven materials the mesh weave areas are inaccessible during sterilization and are potentially a place of microbial contamination and a site of bacterial infection.

All these factors may restrict the use of implants in various clinical cases.

SUMMARY

For purposes of summarizing the disclosure, certain aspects, advantages and novel features of the disclosure have been described herein. It is to be understood that not necessarily all such advantages can be achieved in accordance with any particular embodiment disclosed herein. Thus, the embodiments disclosed herein can be embodied or carried out in a manner that achieves or optimizes one advantage or group of advantages as taught herein without necessarily achieving other advantages as can be taught or suggested herein.

The aim of certain embodiments of this invention is to provide a new implant, method of manufacture and method of use that addresses, reduces, or eliminates one or more of the above said disadvantages and/or fulfills one or more of the desired capabilities mentioned above.

In some embodiments, this task is fulfilled by creating a multi-purpose implant for reconstructing soft tissues, e.g., an implant in which the anti-adhesive properties or control over its integration is determined by the preset surface structure whilst physical and mechanical properties, such as strength and elasticity of the implant, are obtained not by changing the implant's chemical composition, but by virtue of reinforcement element geometry. The multi-purpose implant can be useful in different areas of surgery in operative treatment involving soft tissue deficiency. Embodiments of the disclosed implant are not limited to reconstruction of soft tissue and can be used in any surgical application, including plastic and reconstructive surgery. For instance, disclosed embodiments can be used for hernia repair, neurosurgery, oncology, and others uses.

In some embodiments, the implant is presented in the form of an elastic polymer film (or a patch) from hydrophobic spatially linked (or spatially sutured) polymer based on the methacrylic row oligomers and monomers or any other biologically compatible polymer. The implant also includes a reinforcement element from a polyurethane mesh or other strong and stable woven or unwoven synthetic material. In some embodiments, the reinforcement (or armored) element is partially enclosed by the film so that only the spatially sutured polymer comes into contact with the organs and tissues from the one side only. Depending on the clinical application and goals, the surface area of the reinforcement element can match the surface area of the film and the reinforcement element can be partially enclosed by the film from one side. In other embodiments, the reinforcement element can be cut into separate segments, which can be enclosed by the film from the side, and the aggregate surface area of the segments of the reinforcement element can be smaller than the surface area of the film. The reinforcement element can be non-degradable.

In some embodiments, the surface structure of the spatially sewn or sutured polymer is not porous and is preset during manufacture in compliance with the prospective clinical application. In case two or one surface or any area on the implant surface serves as an anti-adhesive barrier, then a high level of smoothness is set during manufacture. And the reinforcement (or armored) element is partially enclosed by the film so that only the spatially sutured polymer comes into contact with the organs and tissues from the side of the smooth anti-adhesive surface. For example, the surface roughness may not exceed about 50 nanometers, such as be between about 5 and about 20 nanometers. At least the smooth surface can be nonporous so as to prevent or minimize the risk of creating undesired tissue formations (or spikes). The surface of an implant can be inert in order to decrease the reaction of the tissues to the implant. In order to achieve this, the polymer may undergo additional procedure of blocking of free radicals, for example by means of processing of a surface of isopropyl alcohol. Such a level of smoothness prevents the commissure formation (e.g., tunica growth and adhesion, radicular-muscular accretion, etc.) and enables the tissues, contacting with this surface, to move and slide freely.

The production process can exclude the generation of free radicals, which minimizes the triggering of a tissue response.

In some embodiments, where it is desirable for two surfaces or one surface or any area on the implant surface to ensure a strong fixation with adjacent tissues, then the surface is formed as an embossed blind-ended (or not open-ended) pattern or a certain surface roughness is preset. For instance, the surface roughness may be not less than about 10 microns, not more than about 50 microns, etc. The embossed pattern can be made in the form of a mesh, cells, characters, letters, number, and various figures with a preset shape, size and depth. In the post-operative period the adjacent tissues can grow into the cells of this embossed pattern without penetrating the polymer. Thus, in some embodiments, in the post-operative period the tissues that have grown into the tissue cells are unable to shrink, wrinkle, or destroy the implant.

In some embodiments, creation of a surface structure with controllable size, depth and shape of cells makes it possible to control the tissue growth, prevent shrinkage, and avoid infection. Due at least in part to the size and depth of the pores on the surface intended for integration into the tissue, controlled growth of tissue cells and integration of the implant into the body can be achieved, while shrinkage and infection of the pores can be avoided. Research has proven the need for controlling the surface structure of implants used for soft tissue reconstruction, as is described, for instance, in the article "Which mesh for hernia repair?" by C N Brown, J G Finch, published in Ann R Coll Surg Engl. 2010 May (available at http://www.ncbi.nlm.nih.gov/pmc/articles/PMC3025220/), the entirety of which is hereby incorporated by reference.

In some embodiments, the reinforcement element may be woven or unwoven, and of different thickness (for instance, 20-50 microns). The reinforcement element can include synthetic material. It can be made from polyamide, polypropylene, polyethylene terephthalate, polyvinylidene fluoride, or a combination of these materials. The reinforcement (or armored) element is partially enclosed by the film from the side of rough surface so that it is contact with the organs and tissues from the side of the mentioned rough surface of the implant. In places where the reinforcement element is missing, the polymer film can be continuous (or unbroken) or mesh-like or contain holes, such as through holes, of different size and shape. When the size (or surface area) of the reinforcement element matches the size of the implant, the film can have mesh surface or include holes, such as through holes, of different size and shape In some embodiments, the reinforcement element makes it possible to suture and fasten the tissues by a surgical stapler using an elastic polymer film whilst the partial reinforcement of the polymer film enables controlling the implant's physical and mechanical capabilities without changing the polymer's chemical composition, i.e. allows presetting a certain elasticity (radial stretch percentage), strength, and a possibility of suturing in compliance with the clinical application. Some embodiments achieve controlling the strength of the implant and the extent of its stretching not by changing the polymer composition, but by maintaining the geometry, size, and density of the reinforcement element. For example, the strength of the implant can depend at least on the thickness of the reinforcement element.

In some embodiments, the implant can be manufactured by polymerization in molds, in which their surface can be super-smooth (for instance, not more than 50 nanometers) or with a preset topography (embossed pattern). The manufacturing process may use any available polymerization method, such as photopolymerization, thermal polymerization and others. As an example, disclosed embodiments are an improvement over the embodiments described in European Patent Publication No. EP 2644348 titled "A method of manufacturing an artificial elastic implant for restorative and reconstructive surgery," which is incorporated by reference in its entirety. Embodiments of the implants, methods and other features described in EP 2644348 may also be applied to embodiments described in this application.

In some embodiments, a multi-purpose surgical implant for reconstruction of soft tissues includes an outer surface having an elastic film formed from a biologically compatible polymer and a reinforcement element partially enclosed by the elastic film.

The implant of the preceding paragraph may also include any combination of the following features described in this paragraph, among others described herein. The reinforcement element may not contact body organs and tissue during implantation. The biologically compatible polymer can include spatially linked polymer based on methacrylic row oligomers and monomers. The reinforcement element can have a thickness and shape adapted for controlled integration into a body. The surface area of the reinforcement element can be substantially the same as a surface area of the elastic film. The implant can include a plurality of through holes of different size and shape.

The implant of the preceding paragraphs may also include any combination of the following features described in this paragraph, among others described herein. The surface area of the reinforcement element can be smaller than a surface area of the elastic film. One or more regions of the film that do not enclose the reinforcement element can have a mesh surface or include a plurality of through holes of different size and shape. One or more regions of the film that that do not enclose the reinforcement element can be unbroken.

The implant of the preceding paragraphs may also include any combination of the following features described in this paragraph, among others described herein. The reinforcement element can include woven synthetic material configured to stabilize and strengthen the implant. The reinforcement element can include unwoven synthetic material configured to stabilize and strengthen the implant. The reinforcement element can include at least one of polyamide, polypropylene, polyethylene terephthalate, and polyvinylidene fluoride. The outer surface can include a first surface and a second surface opposite the first surface, and at least one of the first and second surfaces can be substantially smooth and non-porous. The at least one of the first and second surfaces can have a roughness that does not exceed about 50 nanometers. The outer surface can be processed so as to block free radicals, thereby decreasing a risk of tissue reaction. The outer surface can be treated with isopropyl alcohol.

The implant of the preceding paragraphs may also include any combination of the following features described in this paragraph, among others described herein. The outer surface can include a first surface and a second surface opposite the first surface, and at least one of the first and second surfaces can include an embossed pattern configured to facilitate fixation with adjacent tissue. The embossed pattern can have a roughness of not more than about 50 microns. The embossed pattern can include at least one of mesh, numbers, and letters.

In some embodiments, a surgical implant includes a non-degradable reinforcement element at least partially enclosed in a polymer film, the film including spatially linked polymer obtained by photopolymerization of methacrylic oligomers and monomers. Photopolymerization can be thermal polymerization.

BRIEF DESCRIPTION OF THE DRAWINGS

Embodiments of the present application will now be described hereinafter, by way of example only, with reference to the accompanying drawings in which.

DETAILED DESCRIPTION

While certain embodiments are described, these embodiments are presented by way of example only, and are not intended to limit the scope of protection. Indeed, the novel methods and systems described herein may be embodied in a variety of other forms. Furthermore, various omissions, substitutions, and changes in the form of the methods and systems described herein may be made without departing from the scope of protection.

Figure 1A:
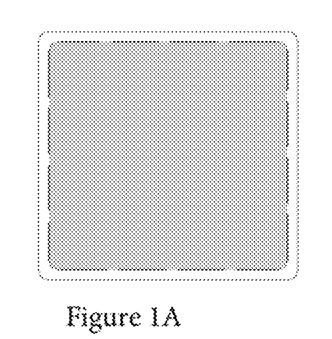
FIGS. 1A-1C illustrate a top view, a profile view and a perspective view, respectively, of an implant according to some embodiments.
Figure 1B:
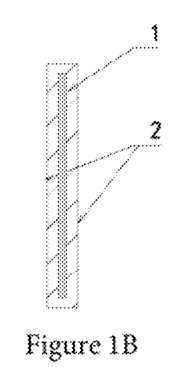
Figure 1C:
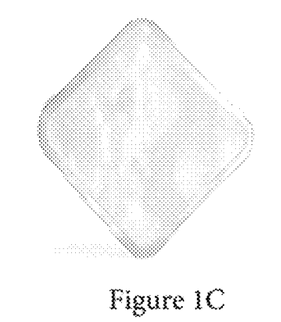

FIGS. 1A-1C illustrate an implant according to some embodiments. The implant of FIGS. 1A-1C is illustrated having a square shape, but it will be appreciated that this and other implants may have any desired shape. The illustrated implant has a profile section with a reinforcement element (1) covered with the film across the entire surface area of the element. The illustrated implant has both surfaces (2) that are smooth. The drawing in the FIG. 1A schematically illustrates the implant, while the drawing in FIG. 1C depicts a manufactured implant.

Figure 2A:
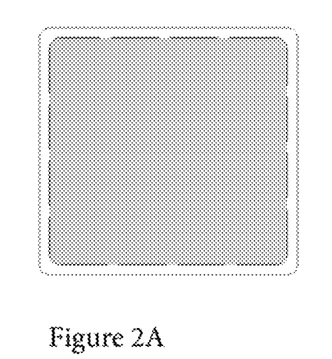
FIGS. 2A-2C illustrate a top view, a profile view and a perspective view, respectively, of another implant according to some embodiments.
Figure 2B:
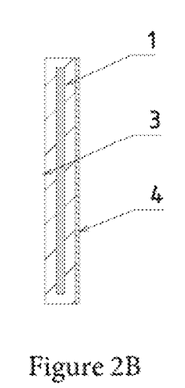
Figure 2C:
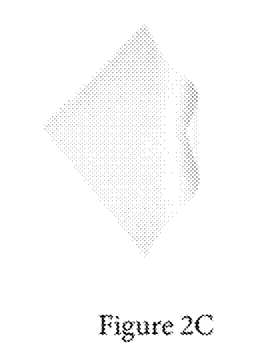

FIGS. 2A-2C illustrate an implant according to some embodiments. The illustrated implant has a profile section with a reinforcement element (1) covered with the film across the entire surface area of the element. The illustrated implant has one surface (3) that is smooth, while the other surface (4) is textured or embossed. The smooth surface (3) can be anti-adhesive so as to minimize tissue adhesion, while the textured surface can promote adhesion and integration into the tissue. The drawing in FIG. 2A schematically illustrates the implant, while the drawing in FIG. 2C depicts a manufactured implant.

The embossed surface (4) can include a pattern of a preset size, depth and cell (or pore) shape. For example, the pattern can include cells measuring about 75 μm (microns) by about 75 μm and be about 50 μm deep. As another example, the cells can measure about 75 μm in diameter and be about 50 μm deep. The cells can have circular, rectangular, hexagonal, or any other suitable shape and can be of any suitable size. The pattern may include cells of more than size and shape. For example, the embossed pattern can be in the form of a mesh, numbers, letters or their combination. The embossed pattern can be regular (e.g., not open-ended). The embossed surface can facilitate fixation to adjacent tissue.

Figure 3A:
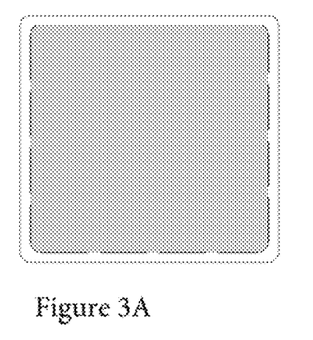
FIGS. 3A-3C illustrate a top view, a profile view and a perspective view, respectively, of another implant according to some embodiments.
Figure 3B:
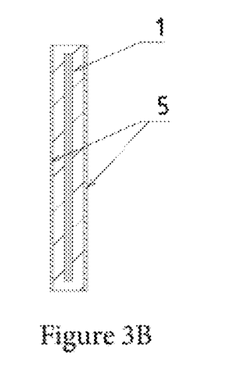
Figure 3C:
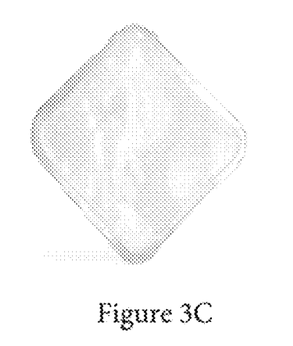

FIGS. 3A-3C illustrate an implant according to some embodiments. The illustrated implant has a profile section with a reinforcement element (1) covered with the film across the entire surface area of the element. The illustrated implant has both surfaces (5) that are textured or embossed. The drawing in FIG. 3A schematically illustrates the implant, while the drawing in FIG. 3C depicts a manufactured implant.

Figure 4A:
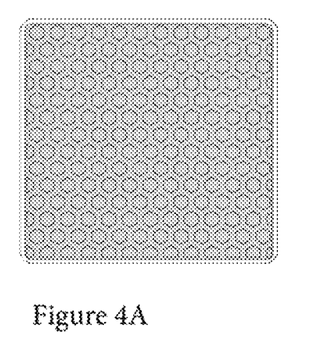
FIGS. 4A-4C illustrate a top view, a profile view and a perspective view, respectively, of another implant according to some embodiments.
Figure 4B:
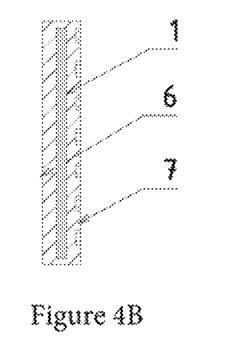
Figure 4C:
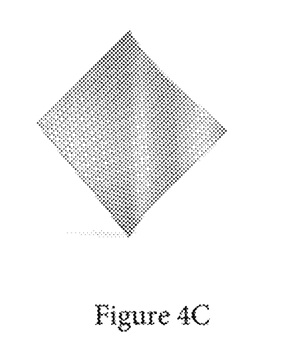

FIGS. 4A-4C illustrate an implant according to some embodiments. The illustrated implant has a profile section with a reinforcement element (1) covered with the film across the entire surface area of the element. The illustrated implant has one surface (6) that is smooth, while the other surface (7) is textured or embossed. The pattern of the textured surface is a pattern of hexagons regularly repeated over the entire surface. The drawing in FIG. 4A schematically illustrates the implant, while the drawing in FIG. 4C depicts a manufactured implant. The textured surface (7) is illustrated by the drawings in FIGS. 4A and 4C.

In some embodiments, the reinforcement element can cover or be embedded in less than the entire surface area of the implant. For example, the implant can include one or more reinforcement element sections. Sections of the reinforcement element can have any suitable shape, such as square, rectangular, circular and radial strip shape. In some embodiments, sections of the reinforcement element can be covered with film on both sides, with the film covering not only synthetic material but also portions extending between sections of the reinforcement element. The film may have the same texture as sections of the implant that do not include the reinforcement element inside the film. In other embodiments, sections of the reinforcement element can be covered with film having different smoothness or texture as sections of the implant that do not include the reinforcement element inside the film. For example, sections of the reinforcement element can be covered with smooth film while other sections of the implant that do not include the reinforcement element have textured film.

Figure 5A:
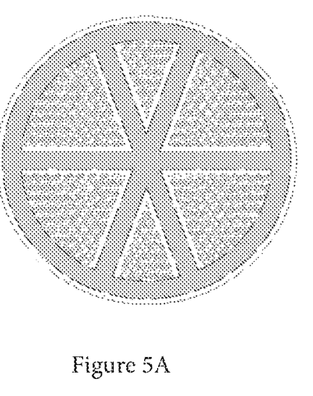
FIGS. 5A-5C illustrate a top view, a profile view and a perspective view, respectively, of another implant according to some embodiments.
Figure 5B:
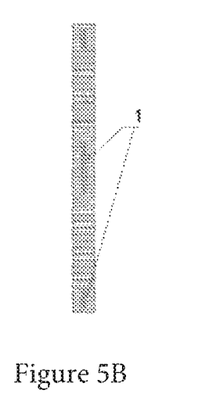
Figure 5C:
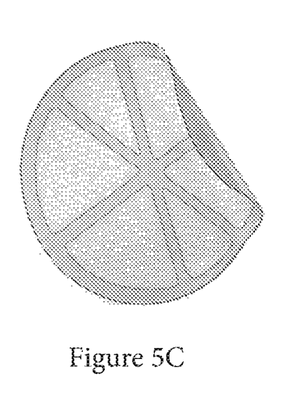

FIGS. 5A-5C illustrate an implant according to some embodiments. The illustrated implant has a profile section with a reinforcement element (1) not covering or being embedded within the entire surface area of the implant. In the illustrated implant, the reinforcement element forms radial rays (or strips) extending from the center of the circle, and the reinforcement element also extends along the periphery of the circle. The reinforcement element can be covered by a polymer film (illustrated as having a circular shape) on both sides. The polymer film may have the same or different texture than the texture of the film in the sections (illustrated as sectors) not having the reinforcement element inside the film. For example, the reinforcement element can be covered with smooth film while other sections having no underlying reinforcement element may have textured film (e.g., such sections may have partially mesh-like texture). The reinforcement element can be cut into desired shapes (e.g., strips and circle) using laser cutting. The drawing in FIG. 5A schematically illustrates the implant, while the drawing in FIG. 5C depicts a manufactured implant. The drawing in FIG. 5C illustrates the textured and smooth surfaces of the implant.

Figure 6A:
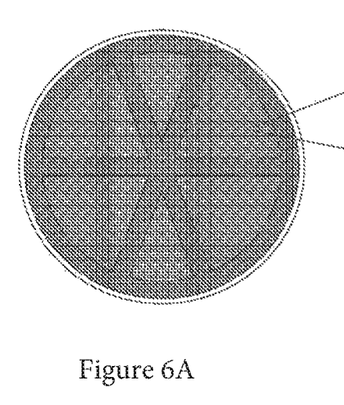
FIGS. 6A-6C illustrate a top view, a profile view and a perspective view, respectively, of another implant according to some embodiments.
Figure 6B:
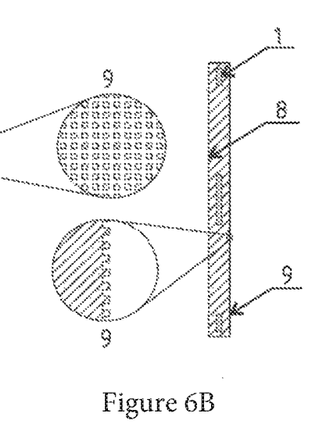
Figure 6C:
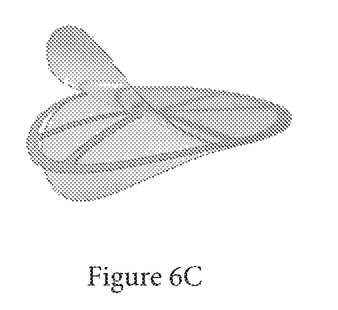

FIGS. 6A-6C illustrates an implant according to some embodiments. The illustrated implant has a profile section with a surface area of a reinforcement element (1) being smaller than the surface area of the implant. In the illustrated implant, the reinforcement element forms radial rays (or strips) extending from the center of the circle, and the reinforcement element also extends along the periphery of the circle (e.g., extends circumferentially). The reinforcement element can be covered by a polymer film (illustrated as having a circular shape) on both sides. The film on opposite sides may have the same or different characteristics. One surface (8) of the implant on one side of the reinforcement element can be smooth, while the other surface (9) on the other side of the reinforcement element can be textured or embossed. The drawing in FIG. 6A schematically illustrates the implant, while the drawing in FIG. 6C depicts a manufactured implant. The drawing in FIG. 6C illustrates a cross-sectional view of the implant and depicts the reinforcement element having radial rays sections extending from the center and a section extending along the periphery of the implant.

Figures 7A, 7B:
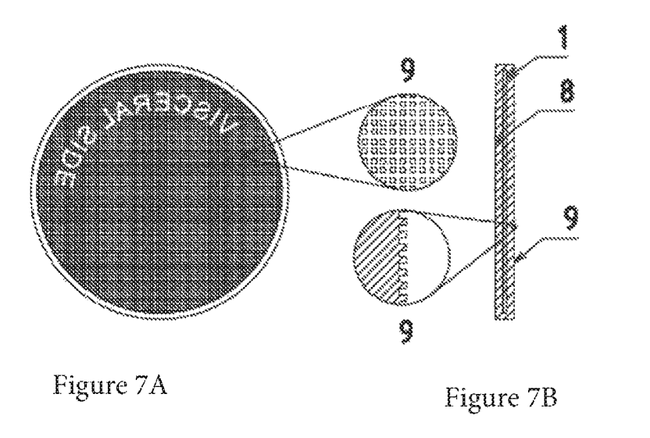
FIGS. 7A-7B illustrate a top view, a profile view and a perspective view, respectively, of another implant according to some embodiments.

FIGS. 7A-7B illustrates an implant according to some embodiments. The illustrated implant has a profile section with a surface area of a reinforcement element (1) covered with the film across the entire surface area of the element. The reinforcement element can be covered by a polymer film (illustrated as having a circular shape) on both sides. The film on opposite sides may have the same or different characteristics. One surface (8) of the implant on one side of the reinforcement element can be smooth, while the other surface (9) on the other side of the reinforcement element can be textured or embossed. The reinforcement element (1) may be solid across a surface area, without holes or apertures, as shown in FIG. 7A, or may have holes as shown in FIG. 6A.

Figure 8A:
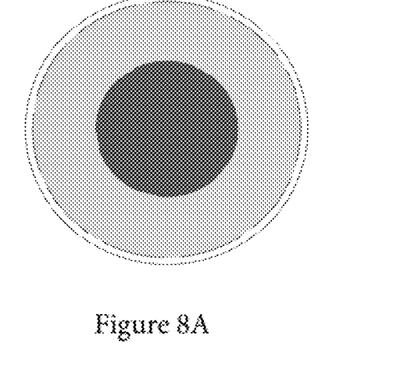
FIGS. 8A-8B illustrate a top view, a profile view and a perspective view, respectively, of another implant according to some embodiments.
Figure 8B:
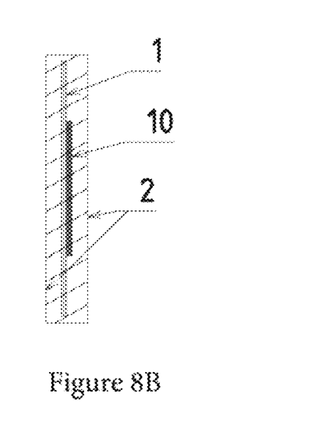

FIGS. 8A-8B illustrates an implant according to some embodiments. The illustrated implant has a profile section with a surface area of a reinforcement element comprising of first reinforcement element (1) and second reinforcement element (10) covered with the film across the entire surface area of the element. The reinforcement element can be covered by a polymer film (illustrated as having a circular shape) on both sides. The illustrated implant has both surfaces (2) that are smooth. The second reinforcement element (10) may be the same size, or smaller than the first reinforcement element.

Figure 9A:
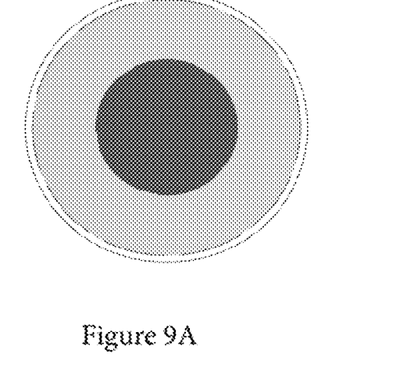
FIGS. 9A-9B illustrate a top view, a profile view and a perspective view, respectively, of another implant according to some embodiments.
Figure 9B:
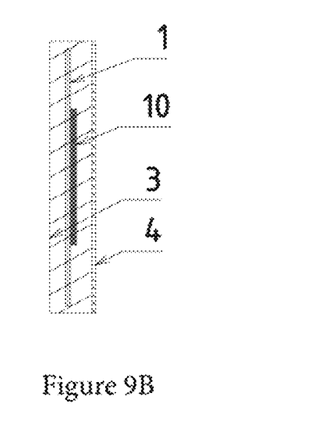

FIGS. 9A-9B illustrates an implant according to some embodiments. The illustrated implant has a profile section with a surface area of a reinforcement element comprising of first reinforcement element (1) and second reinforcement element (10) covered with the film across the entire surface area of the element. The reinforcement element can be covered by a polymer film (illustrated as having a circular shape) on both sides. The illustrated implant has one surface (3) that is smooth, while the other surface (4) is textured or embossed. The smooth surface (3) can be anti-adhesive so as to minimize tissue adhesion, while the textured surface can promote adhesion and integration into the tissue. The second reinforcement element and the textured surface may be on the same side of the first reinforcement element, and on an opposite side of the first reinforcement element than the smooth side.

Figure 10A:
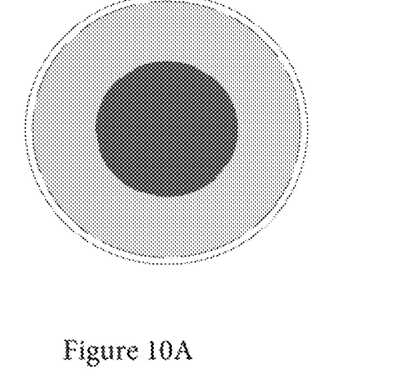
FIGS. 10A-10B illustrate a top view, a profile view and a perspective view, respectively, of another implant according to some embodiments.
Figure 10B:
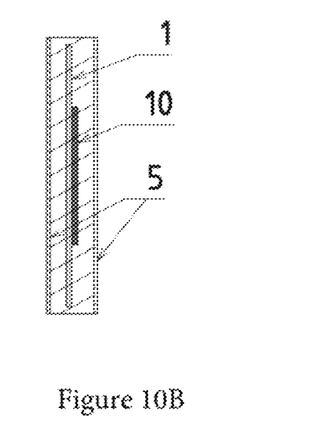

FIGS. 10A-10B illustrates an implant according to some embodiments. The illustrated implant has a profile section with a surface area of a reinforcement element comprising of first reinforcement element (1) and second reinforcement element (10) covered with the film across the entire surface area of the element. The reinforcement element can be covered by a polymer film (illustrated as having a circular shape) on both sides. The illustrated implant has both surfaces (5) that are textured or embossed.

Figures 11A, 11B:
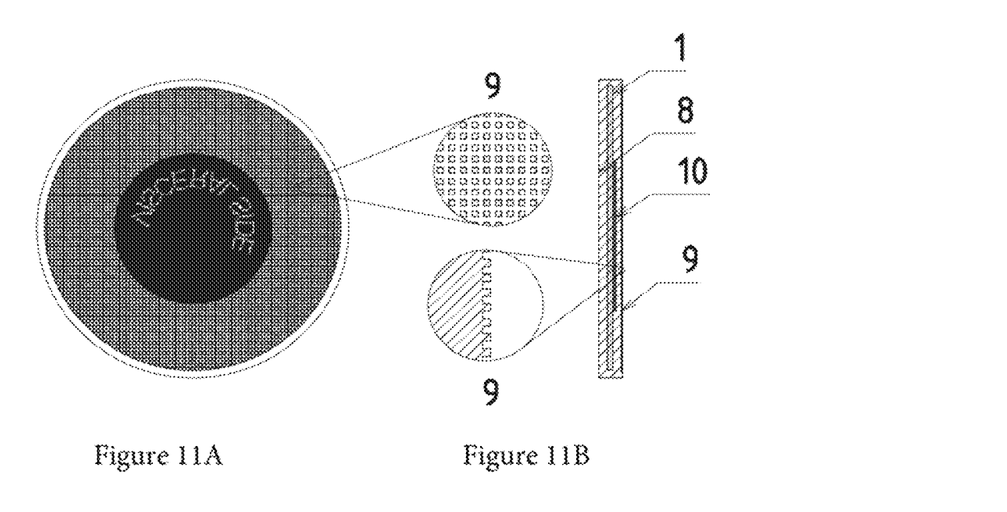
FIGS. 11A-11B illustrate a top view, a profile view and a perspective view, respectively, of another implant according to some embodiments.
Figure 12:
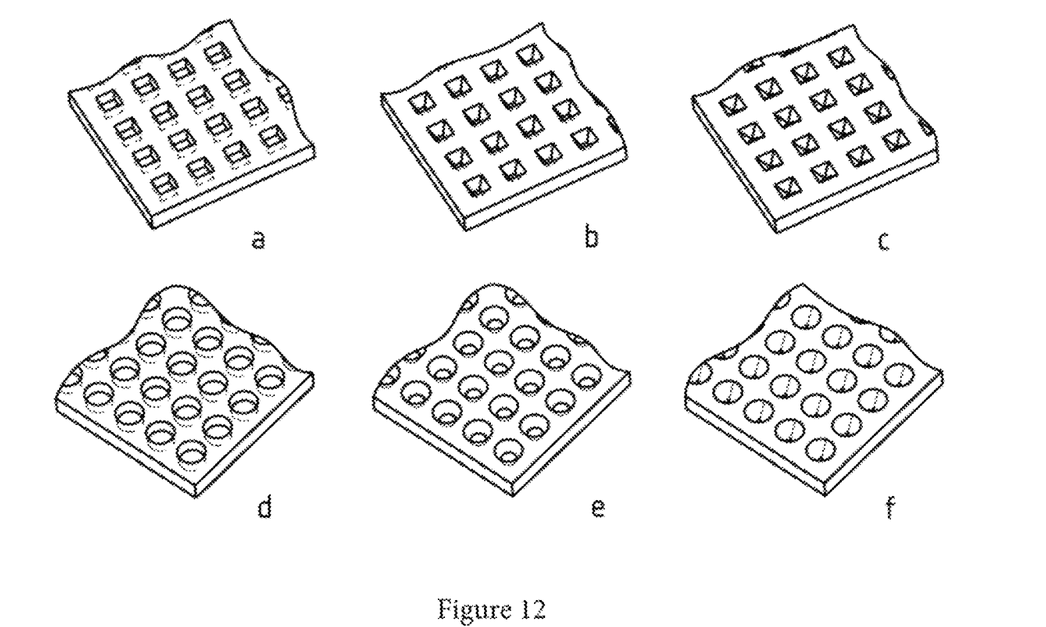
FIGS. 12A-12C illustrate exemplary shapes and forms of texture of the outer surface of the polymer film.

FIGS. 11A-11B illustrates an implant according to some embodiments. The illustrated implant has a profile section with a surface area of a reinforcement element comprising of first reinforcement element (1) and second reinforcement element with cutouts in the form of text (10) covered with the film across the entire surface area of the element. The reinforcement element can be covered by a polymer film (illustrated as having a circular shape) on both sides. The film on opposite sides may have the same or different characteristics. One surface (8) of the implant on one side of the reinforcement element can be smooth, while the other surface (9) on the other side of the reinforcement element can be textured or embossed.

FIGS. 12A-12F illustrates exemplary shapes and forms of texture of the outer surface of the polymer film. For example, the shapes may include rectangular or cubic indentations, square, rectangular, or polygonal pyramid indentations either coming to a point or being truncated, cylindrical, or conical either coming to a point or being truncated.

Figure 13A:
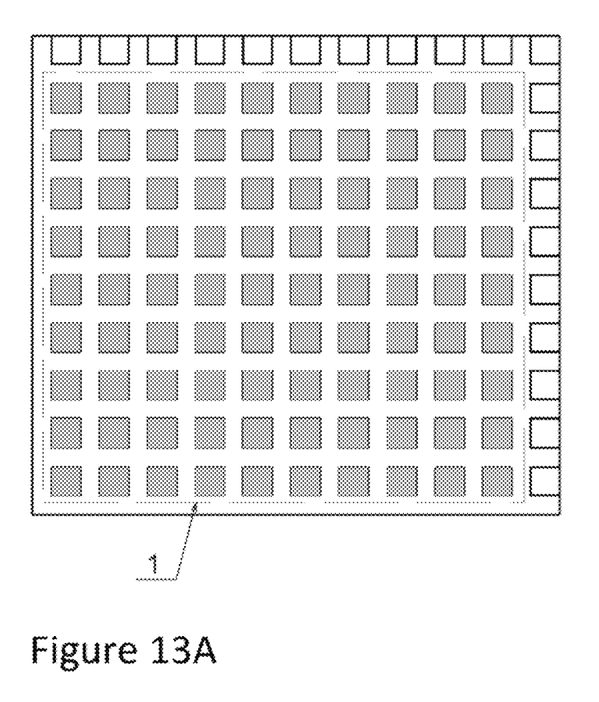
FIGS. 13A-13C illustrate a top view, a profile view and a perspective view, respectively, of another implant according to some embodiments.
Figure 13B:
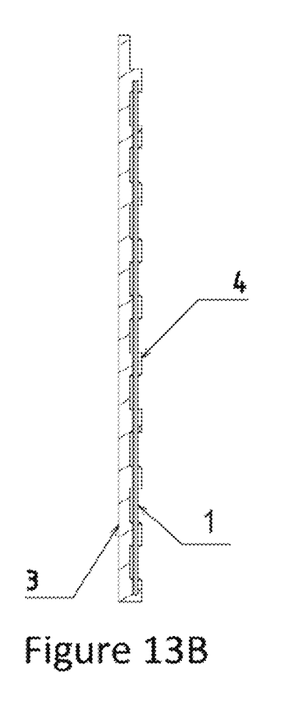
Figure 13C:
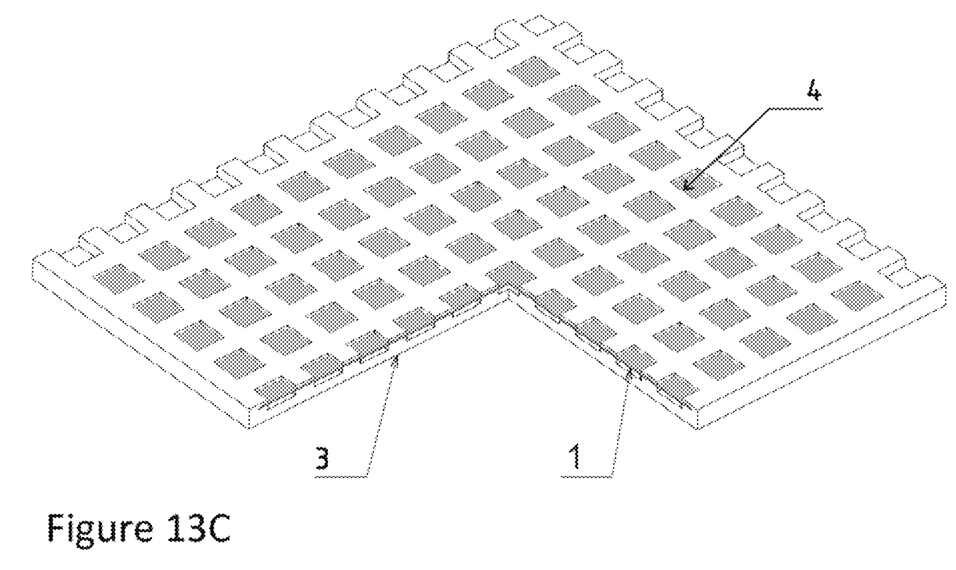

FIGS. 13A-13C illustrate an implant according to some embodiments. The illustrated implant has a top view, profile section with a reinforcement element (1) covered with the film across the entire anti-adhesive surface area of the one side of implant. The illustrated implant has one surface (3) that is smooth, while the other surface (4) is textured or embossed. The smooth surface (3) can be anti-adhesive so as to minimize tissue adhesion, while the textured surface can promote adhesion and integration into the tissue. The drawing in FIG. 13A-13B schematically illustrates the implant, while the drawing in FIG. 13C depicts a view of textured surface (4).

As shown, the textured surface may position the indentations through the reinforcement element, such that the reinforcement element is not fully enclosed. The textured surface may also permit gaps or space to be formed between the one surface (3) and the reinforcement element (1). For example, the implant may include a solid layer, in which a first side of the solid layer defines a smooth surface and a second side of the solid layer defines a textured surface. The textured surface may comprise indentations. The indentations may be any shape, such as rectangular, square, circular, ovoid, etc. and may be uniform along the depth or may be tapered. A reinforcement layer may be integrated with the solid layer such that portions of the reinforcement layer are exposed through the indentations of the textured surface. In an exemplary embodiment, both sides of the reinforcement layer are exposed at the indentations. The reinforcement layer may traverse through all of the indentations or a portion of the indentations. As shown, a partial perimeter of indentations defining the textured surface may extend around a peripheral edge of the implant, where the partial perimeter of indentations does not include a reinforcing layer. The reinforcing layer may also be textured or provide apertures through the reinforcing layer or may be solid.

In an exemplary embodiment, the reinforcement layer may be a woven, solid, or apertured structure. When the reinforcement layer is exposed through the textured surface, the reinforcement layer may form spaces for tissue ingrowth. For example, the reinforcement layer may provide apertures that permit access to the space between the reinforcement layer and the one surface and other apertures in the reinforcement layer to exit the space between the reinforcement layer and the one surface, thereby creating a member for the tissue to hook to. In an exemplary embodiment, portions of the reinforcement layer may be colored or otherwise provide a pattern that is visible or can be felt through the outer surfaces to orient or align the implant during use.

Exemplary embodiments of the multi-purpose surgical implant is formed from an elastic film formed from a non-porous biologically compatible cross-linked copolymer based on 50-75 percent by weight multi-functional urethane (meth)acrylate oligomers and 20-50 percent by weight methacrylate monomers. The elastic film may have a first smooth anti-adhesive surface, and a second relief surface opposite the first surface. The elastic film may be processed by soaking in isopropyl alcohol so as to block residual free radicals, thereby decreasing a risk of tissue reaction. The surgical implant may also have a reinforcement element partially or fully enclosed inside the elastic film, wherein the reinforcement element does not contact body organs and tissue from the side of the first smooth anti-adhesive surface. The reinforcement layer may comprise a plurality of apertures. In an exemplary embodiment, adjacent apertures and an intermediate reinforcement layer portion connecting the adjacent apertures may be exposed through the elastic film. In an exemplary embodiment, the elastic film forms a continuous surface on one entire side of the reinforcement layer. In an exemplary embodiment, the reinforcement layer is raised above an exposed surface of the elastic film. The reinforcement layer may have protrusions supporting and extending through the reinforcement layer to partially encapsulate a portion of the reinforcement layer and to expose a portion of the reinforcement layer. In an exemplary embodiment, a gap is formed between the reinforcement layer and the elastic film continuous layer.

The invention also relates to a method for manufacturing an artificial elastic implant for restorative and reconstructive surgery, comprising two casting steps performed in a casting mold (2, 3). The mold has at least a cover (1) that is optically and UV transparent. In a first step, a first layer of a first photo-curable material or of a second photo-curable material is cast while forming a meniscus (4). Using one of two photo masks (5), the mold is irradiated with UV light to cure the first layer. In a second step, a second layer of either the first or the second photo-curable material is cast onto the cured first layer while forming a meniscus. After irradiating the mold again with ultraviolet light, unhardened photo-curable material is re-moved from the product by dissolving in a suitable solvent. After additionally irradiating the product with UV light, the product is soaked, separated from the mold, placed in isopropyl alcohol for 3 to 24 hours and then vacuum dried.

The first photo-curable material is a composition comprising:
25-40 wt.-% benzyl methacrylate
50-70 wt.-% oligourethane methacrylate
1-5 wt.-% methacrylic acid
1-5 wt.-% octyl methacrylate.

The second photo-curable material is a composition comprising:
   20-30 wt.-% phenoxyethyl methacrylate
   20-30 wt.-% oligourethane methacrylate 1000F
   35-45-wt.-% oligourethane methacrylate 5000F
   1-5 wt.-% methacrylic acid
   1-5 wt.-% ethylene glycol monomethacrylate.

The technical problem to be solved by the invention consists in developing a method that allows to produce an implant, which has high elasticity and minimal impact on the surrounding organs and tissues, which has a high biological stability and providing for areactivity in the post-operative period. The method should also allow producing implants having a uniform surface, either smooth or structured, as well as implants having different partial surfaces, like one smooth and one structured.

This technical problem is solved by a method in accordance with claim 1.

Most of the ingredients used in the method of this invention are commercially available chemicals well-known to the skilled person in the field of polymers. For the oligourethans the following structures apply:

Oligourethane methacrylate 1000F of the following structure:

Moreover the material forms a meniscus in its upper region. A meniscus is a free surface of liquid, the shape of which forms under the influence of gravity and the surface energies of the surfaces involved. The surface of the meniscus will remain very smooth during first curing.

It should be noted, that pouring on the material takes place before the limiting ring is being placed on to the base. That means that the amount of photo polymerizable material must be small enough to avoid the material flowing to the rim of the base and from there down.

The photomask is either the first photomask defining the outer geometrical dimensions of the product to be formed, for example a circular, elliptical or square shape, or the second photomask, which on irradiation forms the structure on the surface of the product and is in the form of numbers, letters, meshes, shapes corresponding to the embossed pattern on the surface of the formed product.

After closing the mold it is irradiated with UV light suitable to photo-cure the material. In this first irradiation it is intended to cure the material all the way from top to bottom of the layer. After irradiation the cover and limiting ring are removed and again photo polymerizable material is being poured onto the object just formed, again while forming a meniscus. The mold is again closed and irradiated.

Oligourethane methacrylate 5000F of the following structure:

This time the photomask is the stencil for the intended surface structure of the product. This may for example be a The casting mold, at least the cover, is made from a material which is transparent for visible light as well as UV light in the spectral region needed for photo polymerization. Suitable materials are UV transparent glass, plastic. The cover can accommodate the photomask into a suitable cavity. The base and the limiting ring can as well be made from other materials like metal, ceramics, plastic. In the present method the mold is not completely filled by the photo polymerizable material.

pattern of shallow dimples or narrow ribs which are to improve the adherence of growing tissue after implantation. It may also be in the form of numbers, letters, meshes, shapes corresponding to the embossed pattern on the surface of the formed product Alternately the first photomask could be used as well in the second step.

After the mold has been opened, excess unhardened photocurable material is being removed by dissolving it in a suitable solvent. In this step the final shape of the product is determined. Suitable solvents include without being limited to, lower alcohols like ethanol, methanol, propanol, i-propanol, ketones like propanone, 4-methyl-pentan-2-one and butanone as well as mixture s of these.

In order to remove all residual monomers which are left in the cured material and could irritate surrounding tissue after implantation, a final UV exposure is now done, followed by soaking the product in hot water of 90 to 100° C. for at least 30 min.

Up to now the product was still adhered to the mold base. It is now separated from the base and placed in the closed container with Isopropanol at the temperature of between −22 and +12° C. for 3 to 24 hours. After vacuum drying the product is ready.

The formulation of the photocurable material is based upon acrylates and is as follows:

The first photo-curable material is a composition comprising
  25-40 wt.-% benzyl methacrylate
  50-70 wt.-% oligourethane methacrylate
  1-5 wt.-% methacrylic acid
  1-5 wt.-% octyl methacrylate.

The second photo-curable material is a composition comprising
  20-30 wt.-% phenoxyethyl methacrylate
  20-30 wt.-% oligourethane methacrylate 1000F
  35-45-wt.-% oligourethane methacrylate 5000F
  1-5 wt.-% methacrylic acid
  1-5 wt.-% ethylene glycol monomethacrylate.

The optimal composition has to be determined by pre-tests.

The formulation advantageously contains other ingredients which are common in the field of photocurable materials. These are for example effective amounts of additives capable of initiation of radical polymerization, optical sensitization and/or inhibiting thermal polymerization, dyes or pigments, stabilizers, and the like. Examples are 3,5-di-t-butyl-o-quinone, azo-bis-isobutyronitrile, 3,5-di-t-butyl-o-quinone and/or 2,2-dimethoxyphenylacetophenone. The invention will be further explained by means of the accompanying drawings, which show specific embodiments of the mold used.

An exemplary mold consists of a base, a cover, and the limiting ring. The upper part of the mold is equipped with a photomask, which is protected by PET-film. A photocurable material is poured onto the base and forms the meniscus on its upper surface.

To manufacture elastic artificial implants for restorative and reconstructive surgery, a casting mold is used consisting of two parts made e.g. of optically transparent material such as glass.

Onto the lower part of the mold the first photo-curable material is poured, consisting of:
  benzyl methacrylate—31.68 wt. %;
  methacrylic acid—1.97 wt. %;
  octyl methacrylate—1.97 wt. %;
  dinitrilazo-bis-isobutyric acid—0.005 wt. %;
  2,2-dimethoxy-phenylacetophenone—0.88 wt. %;
  3,5-di-t-butyl-o-quinone—0.01 wt. %;
  inorganic pigment ultramarine 463—1.0 wt. %;
  oligourethane methacrylate—the rest,
with the formation of the upper meniscus. The base is covered with the upper part of the mold, in which the limiting ring and the photo-mask corresponding to the outer geometrical dimensions of the product to be formed and protected by the PET-film are fixed to the cover. The two parts of the mold are firmly pressed together and irradiated with UV light, the wave length being 360-380 nm, all over the entire surface of the upper part of the mold. The irradiation time is determined empirically so that the curing of the photosensitive composition takes place all the way through the depth of the layer. Then the parts of the mold are separated and onto the lower part of the mold with the layer that has just been formed, the second liquid photosensitive material is poured forming the meniscus, the composition of the second material being:
  oligourethane methacrylate 1000F—25.8 wt. %,
  phenoxyethyl methacrylate—25.6 wt. %,
  methacrylic acid—4.46 wt. %,
  mono methacrylic ethylene glycol ether—4.46 wt. %,
  dinitrilazo-bis-isobutyric acid—0.005 wt. %,
  2,2-dimethoxy-phenylacetophenone—0.775 wt. %,
  3,5-di-t-butyl-o-quinone—0.01 wt. %,
  oligourethane methacrylate 5000F—the rest.

The base is covered with the upper part of the mold on which are fixed the limiting ring and the photo-mask having transparent and opaque areas in the form of numbers, letters, meshes, shapes corresponding to the embossed pattern formed on the surface of the product, protected by PET-film. The two parts of the mold are then firmly pressed together and the mold is irradiated all over the entire surface of the upper part of the mold. Then the mold parts are separated. The product stays on the base of the mold with the remnants of the uncured liquid material that during the time of irradiation was under the opaque areas of the photo-mask. The product is carefully developed in a suitable solvent such as isopropyl alcohol, then the resulting product, without separating it from the mold, is additionally irradiated with UV light for 3-10 minutes in bi-distilled water at T=40-60° C. Then the mold is additionally placed into a container with bi-distilled water and is soaked for 30-45 minutes at a constant T=100° C. Next, the product is separated from the mold and placed in a closed container with isopropyl alcohol for 3-24 hours at the temperature of −20 C to +12° C., after which the product undergoes a thermal vacuum drying at 40-70° C. for 1-6 hours.

This way it is possible to make implants that have two types of surfaces different in structure (FIG. 5): a smooth lower surface, which was in contact with the surface of the base, and a structured surface created by irradiation through the corresponding photomask. This letter surface will after implantation grow together with the adjacent tissue. This smooth surface will not grow together with the tissue and will remain movable. Thus generation of stress around the implant is avoided. In another embodiment of the method of the invention it is possible to provide both surfaces with structure or even both surfaces without the surface structure.

The following working examples and application tests are a further illustration of the method of the invention:

Example 1. To manufacture elastic artificial implants for restorative and reconstructive surgery a casting mold is used consisting of two parts made of glass (FIG. 1).

Onto the lower part 2 of the mold a first light-sensitive material 4 (number 1) is poured, consisting of:
  benzyl methacrylate 31.68 wt. %;
  methacrylic acid 1.97 wt. %;
  octyl methacrylate 1.97 wt. %;
  dinitrilazo-bis-isobutyric acid 0.005 wt. %;
  2,2-dimethoxy-phenylacetophenone 0.88 wt. %;
  3,5-di-t-butyl-o-quinone 0.01 wt. %;
  inorganic pigment ultramarine 463 1.0 wt. %;
  oligourethane methacrylate the rest,
whereby an upper meniscus is formed (FIG. 2). The lower part of the mold with the first light sensitive material is covered with the upper part of the mold on which are fixed the limiting ring 3 and the photo-mask 5, which corresponds to the outer geometrical dimensions of the product to be formed and which is protected by the PET-film 6 (FIG. 3). The two parts of the mold are firmly pressed together and irradiated with UV light of a wave length between •=360-380 nm, all over the entire surface of the upper part of the mold. The irradiation time is determined empirically so that the curing of the photosensitive composition takes place all the way through the depth of the layer. Then the parts of the mold are separated and onto the lower part of the mold with a layer that has just been formed, a second liquid photosensitive material number 2 is poured together with the meniscus. This second material has the following composition:

oligourethane methacrylate 1000F 25.8 wt. %;
phenoxyethyl methacrylate 25.6 wt. %;
methacrylic acid 4.46 wt. %;
mono methacrylic ethilene glycol ether 4.46 wt. %;
dinitrilazo-bis-isobutyric acid 0.005 wt. %;
2,2-dimethoxy-phenylacetophenone 0.775 wt. %;
3,5-di-t-butyl-o-quinone 0.01 wt. %;
oligourethane methacrylate 5000F the rest.

The lower part 2 of the mold is covered with the upper path on which are fixed the limiting ring 3 and the photo-mask 5 (FIG. 4) having transparent and opaque areas in the form of numbers, letters, meshes, shapes corresponding to the embossed pattern formed on the surface of the product to be formed, and which is protected by PET-film. The two parts of the mold are then firmly pressed together and the mold is irradiated all over the entire surface of the upper part of the mold. Then the mold parts are separated. The product stays on the lower part of the mold with the remnants of the uncured liquid material that during the time of irradiation was under the opaque areas of the photo-mask. The product is carefully developed in isopropyl alcohol, then the resulting product, without separating it from the mold, is additionally irradiated with UV light for 3-10 min. in bidistilled water at T=40-60° C. Then the mold with the product is again placed into a container with bidistilled water and is soaked for 30-45 minutes at a constant T=100° C. Next, the product is separated from the mold and placed in a closed container with isopropyl alcohol for 3-24 hours at the temperature of −20 C to +12° C., after which the product undergoes a thermal vacuum drying at 40-70° C. for 1-6 hours. In this way an implant is produced, that has two types of surfaces different in structure (FIG. 5), so the implant does not move on its one side and can move freely on its other side, sliding on the tissues. Such an implant can be used, for instance, in neurosurgery of the brain or spinal cord to reduce the trauma of the tissues and to provide for an areactive postoperative period.

Patient Z., female, born 1947, admitted to hospital 25 Jan. 2008 MLPU "City Clinical Hospital No. 39" of the city of Nizhny Novgorod, with a diagnosis of meningeoma in the left frontal region. 29 Jan. 2008 the patient underwent resection craniotomy, the meningeoma was removed. As a result of the removal of the tumor originating from the dura mater, a 3×3 cm defect of the dura mater was formed. The plasty of the defect was performed using plastic implants for the dura mater plastic defects. The postoperative period went without complications. 13 Feb. 2008 the patient was discharged to outpatient treatment.

Example 2. An artificial elastic implant for restorative and reconstructive surgery is made as in Example 1, but, before the developing takes place, onto the lower part of the mold with the layer that has just been formed, the liquid photosensitive material number 1 is poured to form a meniscus. In this way an implant is produced, which has surfaces different in structure but identical in elasticity (FIG. 5); such an implant can be used, for instance, for complicated neurosurgical interventions on the brain—in case of swelling or dislocation to reduce the trauma of tissues and to provide for areactivity in the post-operative period.

Patient K., male, age 43 was hit by a car Oct. 4, 2008 and admitted to MLPU "City Clinical Hospital No. 39." The MR-tomograms of the patient revealed an acute subdural hematoma in the right fronto-temporo-parietal region, causing a 4 mm dislocation of the brain to the left. Oct. 5, 2008 the patient underwent resection craniotomy in the right temporo-parietal region, and the removal of acute subdural hematoma. After the removal of the subdural hematoma, the brain spread out into the burr window, which formed a TMO defect. Plasty using the implant in question was performed. In the immediate postoperative period the patient's condition slightly improved: the restoration of consciousness to a deep stunning. But 8 days later the patient re-booted into the 1st stage coma. MR-tomography was done again. It revealed a delayed injury—a bruise and crush of the left temporal lobe, causing dislocation of midline structures to the right by 3 mm. Oct. 13, 2008 the patient was subjected to decompressive craniotomy in the left temporo-parietal region, removing the source of injury—a bruise and crush of the left temporal lobe. Plasty of TMO using the implant in question was performed as well. The postoperative period was uneventful. The patient's condition gradually improved and on November 21 in a satisfactory condition he was discharged for outpatient treatment to a neurologist. In the neurological status moderate cognitive and amnestic violations were retained. Feb. 10, 2009 the patient was re-hospitalized for cranioplasty. February 14th the patient underwent Xeno-cranioplasty in both temporo-parietal regions. It should be noted that between the brain, the implant and the overlying soft tissues no scar adhesions had formed, due to which the surgery duration was decreased.

Example 3. An artificial elastic implant for restorative and reconstructive surgery is made as in Example 1, but, before superimposing the upper part of the mold on the lower part of the mold, the liquid photosensitive material number 2 is poured to form the meniscus. This way we receive an implant that has surfaces different in structure but identical in elasticity (FIG. 5): parietal that is intended for contacting with the abdominal wall, and visceral that is intended for contacting with the abdominal cavity, which allows to use it, for example, for reconstructive surgery of the abdominal wall by the intra-abdominal (intraperitoneal) plasty, to reduce the trauma of tissues and to provide for areactivity in the post-operative period.

Example 4. An artificial elastic implant for restorative and reconstructive surgery is made as in Example 1, but, before superimposing the upper part of the mold on the lower part of the mold, liquid photosensitive material number 1 is poured together with the meniscus, then it is covered with the upper part of the mold on which are fixed the limiting ring and the photo-mask having transparent and opaque areas in the form of numbers, letters, meshes, shapes corresponding to the embossed pattern formed on the surface of the product, protected by PET-film, the two parts of the mold firmly pressed together, irradiated all over the entire surface of the upper part of the mold. This way we get an implant having a surface structure that could be penetrated by the connective tissues of the body; this implant can be used, for example, in the surgery of inguinal hernias according to the method of Lichtenstein, to reduce the trauma of tissues and to provide for areactivity in the post-operative period.

Patient S., male, age 52, admitted to MLPU "City Hospital No. 35" 28 Oct. 2007 by emergency service. He was brought in by an emergency team with complaints of severe pain in the right inguinal region, repeated vomiting, the presence of a painful protrusion of the right groin. On examination, he was diagnosed with incarcerated inguinal-scrotal hernia on the right. Based on these emergency indications a surgery was performed—herniotomy using the above-described implant. Smooth post-operative period. Healing by first intention. Suppuration, seromas, infiltrates and fistula were not noted. Discharged in satisfactory condition on day 7. Examined in six weeks. The plasty zone was consistent. No signs of relapse of hernia. An ultrasound scan of the implantation area revealed no liquid formation. The implant was without signs of deformation or dislocation.

Example 5. An artificial elastic implant for restorative and reconstructive surgery is made as in Example 1, but, before superimposing the upper part of the mold on the lower part of the mold, liquid photosensitive material number 2 is poured to form a meniscus, then it is covered with the upper part of the mold on which are fixed the limiting ring and the photo-mask having transparent and opaque areas in the form of numbers, letters, meshes, shapes corresponding to the embossed pattern formed on the surface of the product, protected by PIT-film, the two parts of the mold firmly pressed together, irradiated all over the entire surface of the upper part of the mold. This way we get an implant having a surface structure that could be penetrated by the connective tissues of the body; this implant can be used, for example, in the surgery of inguinal hernias according to the method of Trabucco, to reduce the trauma of tissues and to provide for areactivity in the post-operative period.

Patient B., male, age 57, was admitted on an emergency basis with severe pain in the left inguinal region. He reported that he had had a bilging in this area for many years, which of yesterday stopped going back into the abdomen and became acutely painful. When examined at MLPU "City Hospital No. 35," 28 Nov. 2007, he was diagnosed with incarcerated inguinal-scrotal hernia on the left. Based on these emergency indications a surgery was performed—herniotomy using the above-described implant. Postoperative period went without complications. Seromas, suppuration, infiltration in the area of operations was not observed. The wound healed by first intention. Discharged in a satisfactory condition on day 6.

Example 6. An artificial elastic implant for restorative and reconstructive surgery is made as in Example 1, but after additional irradiation with UV light, the mold is additionally placed into a container of bi-distilled water at constant T=20° C. to soak for 30-45 minutes. Preclinical toxicity study of aqueous extract of the implant according to GOST R ISO 10993-11-2009 by ultraviolet spectroscopy showed the exceeding of the allowable values by 0.2 OP units (the maximum allowed OP value of the aqueous extract is 0.15). No clinical studies were conducted.

Example 7. An artificial elastic implant for restorative and reconstructive surgery is made as in Example 1, but after additional irradiation with UV light, the mold is additionally is placed into a container of bi-distilled water at constant T=100° C. to soak for 3 minutes. Preclinical toxicity study of aqueous extract of the implant according to GOST R ISO 10993-11-2009 by ultraviolet spectroscopy showed the exceeding of the allowable values by 0.12 OP units (the maximum allowed OP value of the aqueous extract is 0.15). No clinical studies were conducted.

In all these examples 1, 2, 3, 4, where the parameters of the method of manufacturing the implant correspond to the invention formula, the implants have high elasticity, a minimal impact on the surrounding organs and tissues, have both the same types of surfaces and the surfaces that vary in texture and smoothness, are of high biological stability, provide for areactivity in the post-operative period. Deviations from the method that strictly follows the invention formula (Examples 6, 7) lead to the formation of the implant that does not have a low enough toxicity, which can have negative effects on living tissue.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. For example, while FIGS. 1-6 depict embodiments that have square or circular shapes, implants may have any other suitable shape. Accordingly, the scope of the present disclosure is not intended to be limited by the specific disclosures of preferred embodiments herein, and may be defined by claims as presented herein or as presented in the future.

The invention claimed is:

1. A multi-purpose surgical implant for reconstruction of soft tissues comprising:
   an elastic film formed from a non-porous biologically compatible cross-linked copolymer based on 50-75 percent by weight multi-functional urethane (meth) acrylate oligomers and 20-50 percent by weight methacrylate monomers, the elastic film having:
   a first smooth anti-adhesive surface, and
   a second relief surface opposite the first surface;
   wherein the elastic film is processed by soaking in isopropyl alcohol so as to block residual free radicals, thereby decreasing a risk of tissue reaction;
   a reinforcement element partially enclosed inside the elastic film, wherein the reinforcement element does not contact body organs and tissue from the side of the first smooth anti-adhesive surface.

2. The multi-purpose surgical implant of claim 1, wherein the first smooth surface has a roughness that does not exceed about 50 nanometers.

3. The multi-purpose surgical implant of claim 1, wherein the elastic film is continuous without apertures such that the reinforcement element is covered with the film across the entire first smooth anti-adhesive surface area of the implant.

4. The multi-purpose surgical implant of claim 1, wherein the second relief surface comprises indentations shaped as cubic, prismatic, or truncated pyramidal with the same depth as a thickness of the elastic film from the reinforcement element to an outer edge of the second relief surface.

5. The multi-purpose surgical implant of claim 1, wherein the reinforcement element comprises a plurality of through holes to improve flexibility during implantation.

6. The multi-purpose surgical implant of claim 5, wherein the elastic film comprises through holes corresponding to the through holes of the reinforcement element such that the reinforcement element is covered by the elastic film across the entire first smooth anti-adhesive surface area of the implant.

7. The multi-purpose surgical implant of claim 1, wherein the reinforcement element comprises unwoven synthetic material.

8. The multi-purpose surgical implant of claim 1, wherein the reinforcement element comprises woven synthetic material.

9. The multi-purpose surgical implant of claim 1, wherein the reinforcement element comprises at least one of polyamide, polypropylene, polyethylene terephthalate, and polyvinylidene fluoride.

10. A multi-purpose surgical implant for reconstruction of soft tissues comprising:
    a polymer elastic film formed from non-porous biocompatible cross-linked copolymer based on 55-75 percent by weight multi-functional urethane (meth) acrylate oligomers and 22-40 percent by weight methacrylate monomers, where the polymer film has a first flat smooth anti-adhesive surface and a second relief surface opposite the first surface with truncated pyramid protrusions, wherein the polymer elastic film is soaked in isopropyl alcohol to block residual free radicals, thereby decreasing a risk of tissue reaction; and
    a continuous reinforcement element partially enclosed inside the polymer elastic film, wherein the reinforcement element does not contact body organs and tissue from the side of the first smooth anti-adhesive surface.

11. The implant of claim 10, wherein the reinforcement element comprises cutouts to improve flexibility of the device during implantation.

12. The implant of claim 11, wherein the polymer elastic film has through holes in areas corresponding to the reinforcement element cutouts to keep the reinforcement element covered by polymer elastic film across the entire first smooth anti-adhesive surface area of the implant.

13. The implant of claim 12, wherein the reinforcement element comprises unwoven synthetic material configured to stabilize and strengthen the implant.

14. The implant of claim 12, wherein the reinforcement element comprises woven synthetic material configured to stabilize and strengthen the implant.

15. The implant of claim 10, wherein the reinforcement element comprises polypropylene.

16. The implant of claim 10, wherein the second relief surface of the polymer elastic film has areas where the protrusions are present and areas where the protrusion are not present form numbers, letters, and combinations thereof.

17. The multi-purpose surgical implant of claim 1, wherein the cross-linked copolymer comprises 50-70 weight percent of oligourethane methacrylate and 1-5 weight percent of octyl methacrylate.

18. The multi-purpose surgical implant of claim 17, wherein the second relief surface comprises an embossed pattern comprising at least one of mesh, numbers, and letters.

19. The multi-purpose surgical implant of claim 1, wherein the cross-linked copolymer comprises 55-75 weight percent of oligourethane methacrylate and 20-30 weight percent of phynoxyethyl methacrylate.

* * * * *